United States Patent [19]

Vieth et al.

[11] 3,972,776

[45] Aug. 3, 1976

[54] PREPARATION OF PROTEIN MEMBRANES CONTAINING MICROBIAL CELLS

[75] Inventors: Wolf R. Vieth, Belle Mead; Shaw S. Wang, Somerset; Rakesh Saini, New Brunswick, all of N.J.

[73] Assignee: Research Corporation, New York, N.Y.

[22] Filed: Feb. 26, 1973

[21] Appl. No.: 336,009

[52] U.S. Cl. ............................ 195/65; 195/31 R; 195/54; 195/57; 195/59; 195/63; 195/68; 195/DIG. 11
[51] Int. Cl.² .................. C07G 7/02; C12K 1/00
[58] Field of Search ............... 195/63, 68, DIG. 11, 195/65, 31, 54, 56, 57, 59; 204/181; 106/161

[56] References Cited
UNITED STATES PATENTS

| | | | |
|---|---|---|---|
| 2,920,000 | 1/1960 | Hochstadt et al. | 106/161 |
| 3,705,084 | 12/1972 | Reynolds | 195/63 |
| 3,709,808 | 1/1973 | Hammond, Jr. | 204/181 |
| 3,758,396 | 9/1973 | Vieth et al. | 204/181 |

FOREIGN PATENTS OR APPLICATIONS

| | | |
|---|---|---|
| 7,017,848 | 6/1971 | Netherlands |
| 953,414 | 3/1964 | United Kingdom |

OTHER PUBLICATIONS

Brown, A.D., The Development of Halophilic Properties in Bacterial Membranes by Acylation Bioch. Mica. et., Biophysica Acts., vol. 93, 1964, pp. 136–142.

Hough, et al., Couplings of Enzymes onto Microorganisms, Nature vol. 235, 1972, p. 389.

Primary Examiner—David M. Naff
Attorney, Agent, or Firm—Oblon, Fisher, Spivak, McClelland & Maier

[57] ABSTRACT

Enzymatically active Protein-whole microbial cell complex membranes suitable for effecting enzymatic reactions are prepared by forming a dispersion containing synthetic polypeptide or natural protein macromolecules and whole microbial cells, casting a membrane from the dispersion and drying the membrane. In an alternative embodiment, the membranes are formed by electro-codeposition from a dispersion containing the macromolecules and cells. It is desirable to pre-treat the microbial cells to destroy proteolytic activity of the cells to prevent the cells from autolyzing and from destroying the membrane.

6 Claims, No Drawings

PREPARATION OF PROTEIN MEMBRANES CONTAINING MICROBIAL CELLS

RIGHTS OF GOVERNMENT

The invention described herein was made in the course of work under a grant or award from the National Science Foundation, an agency of the United States Government, and therefor may be manufactured and used by or for the Government for governmenal purposes without the payment of any royalties thereon or therefor.

BACKGROUND OF THE INVENTION
1. Field Of The Invention

This invention relates to protein-whole microbial cell complexes in membrane form and more particularly to enzymatically active protein-whole microbial cell complex membranes which can be used for catalyzing enzymatic reactions. In another aspect, this invention relates to methods for preparing said enzymatically active membranes and to methods of using said enzymatically active membranes.

2. Description Of The Prior Art

Enzymes are protein catalysts which have been used for a wide variety of industrial and research applications, particularly in pharmaceuticals, paper and textile processing, etc. They are highly specific in their activity and generally do not generate significant quantities of undesirable byproducts. Enzyme reactions are industrially advantageous since they do not require a large investment in heat transfer equipment and can be easily staged, thereby mininmizing the problems associated with interstage product separations.

One problem which has long concerned those dealing with industrial applications of enzymes, however, is the difficulty in separating or recovering enzyme materials. In most commercial processes, the enzymatic rection is effected by simply admixing the enzyme with the substrate, i.e., the chemical being acted upon by the enzyme, and thereafter inactivating and/or recovering the enzyme from the products or the unreacted substrate following the reaction. This procedure, however, has frequently resulted in damage to the product, and inherent loss of large quantities of enzyme, since usually no enzyme is recovered or, if this is attempted, the yields are quite low.

Another problem which has been of significant concern to those engaged in this technology, is that the enzymes usually are used in an aqueous dispersion form. As a rule, however enzymes in this form have a limited shelf life, and, especially, if stored in dilute form, will undergo rapid loss of activity upon storage.

To alleviate these problems, the art has developed various so-called "immobilized enzymes" in which the enzymes are immobilized or bound to inert or insoluble carriers. At the completion of the enzymatic reaction, these insoluble enzyme-containing materials can be separated from the unreacted substrate or product by techniques such as ultrafiltration or the like.

As discussed in Kay, Process Biochemistry, August 1963, which is a synopsis of the history of immobilized enzymes, there have been essentially three known methods of immobilizing an enzyme:

1. covalent bonding onto a chemically modified substrate or onto a substrate capable of covalent bonding;
2. adsorption onto a clay or into a gel, or embedding into an inert matrix (i.e., no bonding);
3. cross-linking the enzyme itself.

All of these prior art techniques, however, have proven to be industrially disadvantageous primarily because the procedures for accomplishing immobilization were complex and required very precise control of pH, temperature, materials and the like.

When an enzyme is chemically modified in preparation for covalent bonding, some of the enzymatically active sites of the enzymes will invariably be chemically attached thereby reducing the activity of enzymes. For instance, Silman et al, Biopolymers, Volume 4, Pages 441–448 (1966), discusses covalently bonding the enzymes to collagen, and p-aminophenylalanine leucine copolymers by use of a diazonium salt. That technique, however, can be shown to produce a product of reduced enzymatic activity.

Adsorption of the enzyme onto a clay or into a gel, or embedding an enzyme into an inert matrix, as taught by Leuschner, British Pat. No. 953,414, also results in products of reduced enzymatic activity, due to the hindrance, or blocking effect, of the matrix.

Cross-linking of an enzyme within itself, such as disclosed by Kay or Silman et al, supra. has similar disadvantages to covalent bonding of enzymes.

In applicant's copending application, Ser. No. 135,753, filed Apr. 20, 1971, applicants had disclosed a new method of immobilizing an enzyme which involved complexing the enzyme with a protein or polypeptide. In one embodiment, it was reported that superior immobilization could be effected simply by casting and thence drying a membrane from a dispersion of protein macromolecules comixed and complexed with an aqueous solution of enzyme In copending applications Ser. No. 176,546 filed Aug. 31, 1971, applicants disclosed a technique of complexing an enzyme with a protein by electrocodeposition.

It was found that direct bonding of the unmodified enzyme to a protein membrane, such as a membrane of collagen or zein, was possible by a complex form of bonding which involved salt linkages, hydrogen bonding and van der Waal forces, and which resulted in a product of superior activity and stability.

Immobilization of enzymes, however, even by the technique as disclosed in applicant's corresponding application, still entailed certain disadvantages, from the point of view that it was still necessary to first extract the enzymes from whole microbial cells, and then recover the enzymes in a purified form. The available techniques for this extraction and recovery generally result in loss of up to 90% of the enzymes, however, so that it would be desirable to provide a technique which would avoid this substantial disadvantage.

Another difficulty with immobilized enzymes is that they tend to lose much of their activity when subjected to elevated temperatures over extended periods of time. Enzymes are in some cases temperature sensitive to an extent that at temperatures as low as 80°C for times on the order of a few minutes, their enzymatic activity will become rapidly deteriorated while immobilization, in general, seems to have a stabilizing effect on activites. Nevertheless, even immobilized enzymes demonstrate a propensity toward degraded activity over time.

It has been known that whole microbial cells exhibit substantial degrees of enzymatic activity, even without separation and purification of the enzyme components of the cell. Heretofore, however, the only known technique of immobilizing whole microbial cells has been by entrapment in an inert matrix (see Mosbach et al, Biotech and Bioeng, XII, 19 (1970)). The difficulty with that technique, however, is that, as with entrapped enzymes, the matrix tends to have an adverse, or hindering effect on the enzymatic activity of the cell.

Other techniques which had been used for immobilizing enzymes were thought to be inapplicable to whole microbial cells, principally because of the larger size of the cells, usually on the order of microns in characteristic dimensions.

Such large particles cannot easily penetrate into the interstices of an immobilizing membrane, so that it was believed that successful chemical bonding would not be feasible.

In the present invention, it has been found that whole microbial cells can be complexed to a protein or polypeptide in membrane form, and in that form will not only provide a higher degree of enzymatic activity than heretofore attainable in the prior art, but will also exhibit a significantly higher temperature stability due to the protective nature of the cell structure.

SUMMARY OF THE INVENTION

Accordingly, one object of this invention is to provide immobilized whole mirobial cells in membrane form and techniques for preparing the same.

Another object of this invention is to provide a technique for effecting enzymatic reactions by passing an enzymatically active substrate over a whole microbial cell-carrier complex membrane, which is characterized by good catlytic activity.

Briefly, these and other objects have now been attained in one aspect of this invention by immobilizing whole microbial cells on protein membranes.

Suitable membranes include both synthetic polypeptides and natural protein. Whole microbial cell immobilization is accomplished by forming a dispersion of the protein, comixing and complexing with it a cell suspension, casting a membrane, and allowing it to dry.

In another embodiment, whole microbial cells are complexed with protein macromolecules by electrocodeposition from a bath, to form an enzymatically active membrane.

The complexing mechanism between whole microbial cells and protein membranes or film-like protein carriers involves the formation of multiple hydrogen bonds, salt linkages, and van der Waals interactions. Complex formation is facilitated at a pH between the isoelectric points of the whole microbial cell and the protein membrane.

DESCRIPTION OF THE PREFERRED EMBODIMENTS

Any of a wide variety of synthetic polypeptides and natural proteins may be used in forming the membrane portion of the complex. For instance, suitable natural proteins include collagen, zein, casein, ovalbumin, wheat gluten, fibrinogen, myosin, mucoprotein, and the like. Suitable synthetic polypeptides include polyglutamate, polyaspartate, polyphenylalanine, polytyrosine, and copolymers of leucine with p-amino phenylalanine and the like. Collagen and zein are preferred natural protein materials.

The selection of a particular synthetic polypeptide or natural protein, will be largely determined by the nature of the enzyme being complexed, the substrate to be treated, and the reaction environment to be encountered.

Suitable whole microbial cells which may be used in this invention include:

Bacteria, particularly acetobacter, lactobacillus, clostridium and pseudomonas, such as suboxydans, acetixylinum and the like; delbruecki, suboxydans and the like; acetobutylicum and the like; hydrophila and the like.

Also, actinomycetes, particularly streptomyces, such as phaechromogenes, griseus, and the like.

Also, moulds or fungi, particularly aspergillus and penicillium, such as niger, oryzae, and the like; notatum, griseofulvum, funiculosum, bilacinum and the like.

Also yeast, particularly saccharomyces and torula, such as cerevisiae, ellipsoideus, and the like; torulopsis, utilis and the like.

These whole mirobial cells may contain a wide variety of different enzymes which are membrane bound enzymes, intra-cellular or endo enzymes and essentially all the enzymes involved in cellular metabolism. These enzymes include adenosintriphosphatases, hydroxymethyl-glutaryl coenzyme A reductase; the mitochondrial enzymes such as pyruvic oxidase complex, and acyl-coenzyme A synthetase; other membrane bound enzyme such as adenylcyclase and phosphodiesterase; intracellular enzymes of the glycolytic pathway such as alcohol dehydrogenase, lactic dehydrogenase, aldolase glucose-6-phosphate isomerase, and the like; enzymes of the pentose phosphate pathway such as glucose-6-phosphate dehydrogenase, transketolase, transaldolase, and the like; enzymes of the fatty acid synthetase complex, such as malonyl CoA synthetase; D-sorbitol dehydrogenase, gluconolactonase, 3-keto steriod $\Delta'$ dehydrogenase, 11-$\alpha$-progesterone hydroxylase, 9-$\alpha$-fluorocortisol hydroxylase, xylose isomerase, $\beta$-galactosidase, penicillin amidase, tryptophan pyrrolases, sucrose 6-glucosyl transferase, glucoamylase glucose oxidase, galactose oxidase; enzymes of nucleic acid metabolism such as dihydro-orotase, glutamic synthetase, folic reductase, dihydrofolic reductase, penicillinase, and ethanolamine oxidase.

Invertase of $\beta$-D-fructofuranosidase is widely used in the food and beverage industires, as well as for analytical purposes. Invertase can be used to catalyze the hydrolysis of sucrose to glucose and fructose or invert sugar. Invertase is effective in the hydrolysis of $\beta$-D-fructofuranosyl linkages in sucrose, raffinose, gentianose, and methyl and $\beta$-fructofructose. One particularly important application for an immobilized whole mirobial cell containing invertase is in the continuous hydrolysis of sucrose.

$\alpha$-amylase is referred to as a "liquifying enzyme" and is known to randomly hydrolyze starch, glycogen, and dextrans. B-amylase can produce maltose from sugar, glycogen and dextran. Other suitable amylases incluce $\alpha$-glucosidase, amyloglucosidase, amylo-1,6-$\alpha$-glucosidase (debranching enzyme), oligo-1,6-glucosidase (limit dextrinase), isomaltase, and isotriase. As used herein, the term "amylase" refers generically to one or more of these and other amylases. One particularly important application of an immobilized whole cell containing amylase is in the continuous hdyrolysis of starch.

Immobilized complexes formed in this manner provide good enzymatic activity. When an enzymatically active substrate is contacted with such complexes, the degree of enzymatic activity tends to remain constant and there is no necessity to provide a separate separation procedure, as in the prior art.

In preparing the complexes of this invention, it is necessary to "fix" the cells. That is, the whole cells should be maintained in a stationary phase such as by heat treatment to a temperature of 60° to 80°C for one minute to two hours and/or by adding uncouplers such as 2,4-dinitrophenol, pentachlorophenol, other highly substituted lipid soluble phenols, gramicidin, and dicoumarol. When spores are used, as the whole cells, fixing can be dispensed with since spores are in a resting stage.

The whole microbial cells to be immobilized are dispersed in a suitable inert medium, such as water. Good reslts are attainable when the solids content of the dispersion is between 0.5 and 10% by weight. The protein is contained in the dispersion in amounts of from about 0.1 – about 5% by weight. The concentration of protein will, of course, depend upon the particular protein being used. For instance, when collagen is the protein, the suspension will tend to become too viscous if greater than 1% by weight is used. Preferably, the protein is used in amounts of 0.1 – 1.0% by weight.

The temperature of pre-treatment of the cell suspension is quite important, since it is necessary to destroy the proteolytic activity of the cells. If the proteolytic activity is not destroyed, the cells will tend to autolyze and also will tend to destroy the structural integrity of the protein membrane. It has been found that effective destruction of proteolytic activity is obtained if the cell suspension is heated to a temperature of from 80° to 82°C for at least 10 minutes. Longer periods and higher temperatures are also effective, but if the temperature is raised to above 90°C there may be adverse effects on the quality of the cells.

The protein carrier is dispersed by any conventional technique. A suspension of whole cells is then comixed and complexed with it, after which a complex membrane is cast and dried. Good reslts are attainable when the thickness of the membranes used is from 6 to 20 mils.

Th pH of the dispersion at the time of contact should correspond to the type of whole cell being used and can be within a range of 2 to 12. If the whole cells contain an alkaline enzyme, the pH of the dispersion should be alkaline, and if the enzyme is acidic, the pH of the dispersion should be acidic.

At the termination of the drying period, the whole microbial cells will have become bonded to the membrane. Bonding will be a multiple bonding mechanism which includes at least salt linkages, van der Waal forces and hydrogen bonding. One important aspect of this invention is the fact that the microbial cells are bonded directly to the protein of the membrane. Unlike the prior art techniques of bonding enzymes to protein materials, the whole cells are not prior diazotized, nor is the membrane diazotized, nor are the protein material or whole cells otherwise treated chemically to produce covalent linkages. In the present invention, the whole cells are contacted with the protein macromolecules and it has been found that bonding occurs directly. The reaction might be loosely analogized to reconstitution of a primitive tissue by combining fibrous protein and whole cells bonded by physicochemical bonds.

The resulting product is an enzymatically active membrane which is characterized by good structural integrity. Moveroer, since whole microbial cells are characterized by a high concentration of enzymes, the enzymatic activity of the membrane containing the immobilized whole microbial cells is higher than previously attainable by immobilizing enzymes to protein membranes. Moreover, it has been found that the retained skeleton of the cells seems to have a significant temperature stabilizing effect on the enzymes such as provided in the following example:

Two reactors, one packed with immobilized whole cells (*Streptomyces Phaeochromogenes* containing active glucose isomerase) and the other packed with immobilized glucose isomerase (enzyme extracted from *Streptomyces phaeochromogenes* cells and purified) were operated continuosly at 70°C for a time period on the order of months. Immobilized whole microbial cell complex had glucose isomerase activity of 290 units/gram product and immobilized enzyme was found to have 80 units/gram product. Regarding the temperature stabilizing effect, immobilized whole cells had a half life of 60 days whereas the immobilized enzyme derivative had a half life of only 20 days. (Half life is defined as the time at which the immobilized preparation reaches half of its initial activity.) The particular technique and apparatus which may be used for the electrocodeposition process is the same as disclosed in said copending application Ser. No. 176,546.

The use of immobilized whole cells can also be shown to be very fruitful when a number of enzymes are required for a given process. A special advantage is involved when a process requires cofactors, such as NAD/NADH+ H+. In these cases, the cells are not only used as a source of enzyme or enzymes, but also as a source of cofactors.

In one embodiment, collagen was used as the membrane material. Collagen is a fibrous hydroxyproline, glycine-type protein, which is the chief organic constituent of connective animal tissue and bones. In this embodiment, collagen either from cow tendon or cow hide, is blended into dispersion in a Waring blender. The pH of the dispersion was adjusted to acidic or basic condition depending upon the particular enzyme involved. The concentration of collagen in the dispersion is usually between 0.5 to 5% wt./wt. at this stage. A cell suspension is then added to the dispersion in the Waring blender, and further blended. The ratio of cell to collagen (dry weight basis) is between 1/5 to 3/1, depending on the type of cells; e.g., spherical, rod, filamentous, etc. The well-blended mixture is then cast on a Mylar background, producing a wet thickness of 100 to 500 mils. The cast membrane is allowed to dry on the Mylar at room temperature. The dried film is then tanned by dipping in acidic chromium sulfate solution (11.67%, aged at least one month) (acid enzyme), or in alkaline formaldehyde solution (10 %HCHO, 1%NaHCO$_3$) or glutaraldehyde solution, etc. (alkaline enzyme). Tanning time is usually between ½ minute and ½ hour, depending on the stability of the enzyme involved in the tanning solution. The tanned membrane is then washed thoroughly in running water for at least ½ hour. The membrane is then ready for use. The membrane can be stored either dry or wet. The thickness of the dried membrane is usually between 2 to 10 mils or 0.005 mm to 0.1 mm.

The cell-collagen complex medium should be carefully dried preferably at about room temperature or below, so as not to damage the bound cells.

The membrane which contains immobilized whole cells is usually layered on an inert background such as rayon-cotton mixed fabric and rolled up as a cylindrical cartridge. The thickness of the inert background is usually between 5 to 20 mils.

Usually a central rod is used to start construction of the cartridge which is then fitted snugly into a jacketed column or other kind of housing to form a catalytic reactor.

While collagen is used as a preferred example for the above description of the art, other membrane forming materials such as zein, and other dispersible natural polymers or synthetic polymers can also be used as carriers for immobilizing whole cells in a membraneous form.

As a second example of using natural protein to complex microbial cells, a zein whole cell film is prepared by casting a solution of zein and whole cells according to state of the art techniques. The same procedure was used to prepare protein-cell complexes as was done with collagen film.

Zein is the prolamin (alcohol-soluble protein) of corn. It is the only commercially available porlamin and one of the few readily available plant proteins. Zein occurs primarily in the endosperm of the corn kernel. The amount of alcohol-soluble protein is directly related to the total endosperm protein content, with zein contents ranging from 2.2 to 10.4% of the dry substance in various corn samples.

Zein is characterized by a relative deficiency of hydrophilic groups in comparison with most proteins. In fact, the high proportion of nonpolar (hydrocarbon ) and acid amide side chains accounts for the solubility of zein in organic solvents and its classification as a prolamin.

One of the commercial zeins is Argo Zein G-200, manufactured by Corn Products Refining Company, Argo, Illinois. Film casting solutions can be formulated on a pure components basis, taking into account the water content of the raw zein and other reagents. The casting solutions are prepared by dissolving the protein in the organic solvent of choice by gentle stirring, at room temperature, for a period of 1-2 hours, during which period solution is complete. Examples of suitable solvents which may be employed include 81% (wt./wt.) isopropyl alcohol and 4% methyl cellosolve (ethylene glycol monoethyl ether). The clear solutions, which contained 20–30% by weight of dry zein, are of amber color. Curing agents, such as formaldehyde, and a plasticizer may be added shortly before film casting.

Of course, any one of the many state of the art techniques can be used to form suitable zein casting solutions, and the above description is only exemplary of one suitable prior art technique.

Another method of preparing enzymatically active protein-whole microbial cell complex membranes is by electrocodeposition from a macromolecular protein dispersion, comixed and complexed with whole microbial cells having enzymatic activity. The microbial cell walls are composed in part of polypeptides, thus the cells have a net electrical charge depending upon the pH of the cell suspension.

On mixing a dispersion of suitable protein carrier material with an aqueous suspension of whole microbial cells, stable macromolecular complexes between the cells and the protein are formed. These cell-protein macromolecular complexes have a net electrical charge at a pH on either side of their isoelectric point and would migrate under the influence of an electrical field. On drying the complexes, after a suitable thickness of the macromolecular complexes have electrically codeposited, an enzymatically active membrane form containing immobilized whole microbial cells results. Both the cells and carrier material need not exist in charged form since they form complexes in dispersion, hence either the cell or carrier, if in charged form, will provide a net electrical charge for the complex.

Having now generally described the invention, a more detailed understanding of the invention can be attained by reference to certain specific examples which are provided herein for purposes of illustration only, and are not intended to be considered as limiting of the invention unless otherwise so specifically indicated.

EXAMPLE 1

To 20 grams of frozen *Streptomyces phaeochromogenes* cells (batch number 6-7-72), distilled water was added to bring the volume of the suspension to 100 mls. The suspension was stirred for 10 minutes to disperse the cells. The cell suspension was heated at 80°C for 15 minutes with shaking (130 RPM) on a Gyrotory water bath shaker and the suspension was then cooled slowly to room temperature.

One hundred and ten grams of hide collagen was added to 100 ml of water and blended in a Waring blender. The pH of the blended mixture was adjusted to 11.2 by adding 1 N NaOH solution. The resulting cell suspension was then slowly blended into the collagen dispersion. The mixture was cooled intermittently to prevent a rise in temperature above 20°C. The mixed dispersion was cast onto a Mylar sheet and then dried to room temperature. Total dry weight of the complex was 12.5 grams. The dried complex was tanned in formaldehyde solution [10% (w/v), containing 1% sodium bicarbonate, pH 8.35] for one minute. It was then washed immediately for half an hour under cold running water. 1.23 gms of the tanned complex membrane was cut into small chips which were assayed for glucose isomerase activity. The chips ¼ inch × ¼ inch in dimension, were used to catalyze the isomerization of 5 mls of 18% glucose (containing 0.01 Molar $Mg^{++}$ and 0.2 Molar pH 7 phosphate buffer) at 70°C. The reaction was carried out in a test tube placed on a shaker and maintained at 70°C. Shaking was adjusted to a speed of 150 cycles per minute. The reaction was followed by noting the amount of fructose formed using the thiobarbituric acid method (2). The assay method was modified and automated for use on the Autoanalyzer (Technicon Instruments Corporation, Tarrytown, New York). Percent of glucose converted to fructose was noted at different reaction times. Table 1 summarizes the results. From the initial conversion data it was calculated that *Streptomyces phaeochromogenes* cells equivalent to 131 units of glucose isomerase activity were immobilized per gram of the complex. A unit was defined as the amount of enzyme which produced 1 mg. of fructose per hour at 70°C.

Table 1

| Time (hours) | Percentage Conversion |
| --- | --- |
| 0.5 | 9.0 |
| 1.0 | 16.6 |
| 1.5 | 23.5 |
| 2.0 | 30.1 |
| 4.0 | 42.1 |
| 5.5 | 45.0 |

EXAMPLE 2

This example demonstrates the tanning of collagen-cell complex membrane in formaldehyde solution for varying lengths of time. The cross-linking of the membrane results in stable complexes which can be used at high temperatures (up to 70°C).

Distilled water was added to 33 gms of frozen *Streptomyces phaeochromogenes* cells (batch number 6-29-72) until the volume of the suspension was 200 mls. The suspension was magnetically stirred for 15 minutes in order to well disperse the cells. The cell suspension was heated for 1 ½ hours at 80°C on the gyratory water bath shaker (130 CPM).

The suspension was added to 150 gms hide collagen and the collagen-cell complex was magnetically stirred. The pH of the mixture was slowly changed with continued stirring to 11.35, using drop by drop addition of 1 N NaOH. (Slow addition of dilute sodium hydroxide with high speed magnetic stirring prevents local pH rise in the mixture above the desired value.) During the 2 hour period of stirring, a rise in temperature of the mixture above 20°C was avoided. The dispersion was cast onto a Mylar sheet and permitted to dry at room temperature.

A small portion of the dried complex membrane was cut and divided into seven pieces. Each piece was weighed and tanned for different lengths of time in liquid formaldehyde [10% (w/v), containing 1% sodium bicarbonate, pH 8.35]. Immediately afterward, each piece was washed under cold running water for half an hour. Also the non-tanned piece was washed for one-half hour. Each piece was then assayed for glucose isomerase activity at 70°C using 10 mls of 18% glucose (containing 0.01 M $Mg^{++}$ and 0.1% methyl paraben) as substrate. The reaction was conducted in test tubes with shaking (130 CPM). By measuring the amount of fructose formed in half an hour, the units of enzyme on each piece are calculated. Table 2 summarizes the results:

Table 2

| Weight of Complex (gms) | Tanning Time (minutes) | Total Units of Glucose Isomerase | Units gm. complex |
| --- | --- | --- | --- |
| 0.42 | 0.0 | 54.0 | 128.5 |
| 0.29 | 0.5 | 80.4 | 268.4 |
| 0.35 | 1.0 | 71.4 | 201.0 |
| 0.26 | 2.0 | 64.2 | 249.0 |
| 0.45 | 5.0 | 93.6 | 207.6 |
| 0.47 | 10.0 | 25.6 | 54.6 |
| 0.38 | 30.0 | 4.8 | 12.7 |

EXAMPLE 3

Using 66 gms of frozen *Streptomyces phaeochromogenes* cells (batch number 6-29-72) suspended in 200 mls of water, and 210 gms hide collagen, collagen-cell complex membranes were prepared by the procedure described in Example 2. The membrane was then tanned in formaldehyde solution followed by half-hour washing in cold running water.

25 gms of the complex membrane were layered over a 5-inch wide VISKON filter fabric (code number 3362, style SK 350-CM, Chicopee Mills Inc., 1450 Broadway, New York) which served as a spacing element. A 5-inch long and 3mm in diameter glass rod, was used as the central element. The collagen-cell membrane complex was coiled upon the filter fabric (6 mil thick) to form two cartridges. Each cartridge was 5 inches long and 1 inch in outside diameter. The filter fabric provided a very efficient contact between substrate and membrane and prevented overlapping of the membrane layers.

The two cartridges were packed back to back in a jacketed glass column. The column dimensions were 11.5 inch jacketed length and 1 inch internal diameter. The column had indentations in the bottom on which the cartridges were supported. The column was also provided with a pre-heat section to bring the substrate solution to the proper temperature before it contacted the catalyst bed. The temperature in this system was controlled by circulating water through the reactor jacket at a high flow rate, using a constant temperature circulator (Haake Instruments, Inc., Model FJ). In this way, the reactor temperature could be maintained constant within ±0.2°C. The column was used to isomerize glucose continuously which was supplied at the bottom of the column by a peristaltic pump. The liquid flowed upward through the column and the product was collected from the top of the column. In this flow-through reactor configuration, the uniform laminar flow pattern over the membrane surfaces was facilitated by the capillary action of the filter cloth spacer and the small pressure developed by the peristaltic pump. The transport of reactant and product into and out of the membrane complex then proceeded by diffusion. Thus the cell-membrane complex was contacted efficiently.

The column was operated at 70°C. The substrate used was 18% glucose containing 0.01 Molar $Mg^{++}$ and 0.1% Methyl paraben. No buffer was used in the substrate and the pH of the substrate was adjusted to 7.1 using 1 N NaOH. The void volume in the column was about 20cc and the flow rate varied between 11 mls/hours to 12 mls/hour. These numbers correspond to a residence time of about 1.7 to 1.8 hours in the column. The results are summarized in Table 3:

Table 3

| Sample Time | Percent Conversion |
| --- | --- |
| 4 hours | 41.0 |
| 5.5 hours | 42.5 |
| 31 hours | 40.0 |
| 53 hours | 40.0 |
| 79 hours | 41.8 |
| 4 days | 40.6 |
| 5 days | 40.6 |
| 6 days | 41.0 |
| 7 days | 39.7 |
| 8 days | 38.4 |
| 10 days | 35.4 |
| 11.12 days | 35.0 |
| 12 days | 35.0 |
| 13 days | 38.4 |
| 14 days | 38.5 |
| 15 days | 40.0 |

The column continued to isomerize glucose continuously even after several weeks from the termination of daily measurements.

EXAMPLE 4

This example demonstrates the preparation of enzymatically active protein-whole microbial cell complex membrane by electrocodeposition.

0.75 grams of sodium alginate dissolved in 75 ml. distilled water were added to 100 cc of 1% collagen dispersion. Concentrated TRIS solution was added to it drop by drop with continued magnetic stirring until the pH was 8.5 and the mixture was well dispersed. One gram of dried *Streptomyces phaechromogenes* cells was mixed with the dispersion using high speed magnetic stirring.

The dispersion was put into a stainless steel vessel which was used as a cathode. A flexible stainless steel screen was placed in the middle of the electrocodeposition vessel and connected, as an anode, to the power supply. On applying a direct current of 0.5 – 0.6 amperes at a voltage of 50, the whole cell-collagen complexes started depositing on the flexible stainless steel anode. After 15 minutes deposition, the power supply was shut-off, and the anode was taken out of the vessel. The membrane was allowed to dry on the electrode. Repeating this procedure, a total of 3.6 grams (dry weight) of whole cell-collagen complex membrane was deposited on 9 stainless steel screens.

These screens, with the membrane coated on them, were packed in a glass housing provided with an inlet and outlet. The module was used to catalyze the conversion of glucose to fructose by passing the substrate solution over the active membrane containing immobilized whole microbial cells. The module was operated three times at 60°C in a recirculation style with washing after each run. Each time the immobilized whole microbial cells containing glucose isomerase were found to be active, as evidenced by a substantial (13%) conversion of glucose to fructose.

Having now fully described the invention, it will be apparent to one of ordinary skill in the art that many modifications and variations can be made without departing from the spirit or scope of the invention. Accordingly, what is intended to be covered by letters patent is:

What is claimed as new and desired to be secured by Letters Patent of the United States is:

1. A process for producing an enzymatically active membrane, which comprises the steps of:
    dispersing whole microbial cells in an inert solvent medium such that said dispersion contains from 0.5% to 10% by weight whole microbial cells;
    heating said dispersion of whole microbial cells at a temperature of 80° to 90°C for at least 10 minutes to destroy the protoelytic activity of said cells;
    dispersing a protein selected from the group consisting of collagen, zein, casein, ovalbumin, wheat gluten, fibrinogen, myosin and mucoprotein, or a polypeptide selected from the group consisting of polyglutamate, polyaspartate, polyphenylalanine, polytyrosine and a copolymer of leucine and p-aminophenylalanine in an inert solvent medium such that said dispersion contains from 0.1% to 5% by weight protein or polypeptide;
    adjusting the pH of said dispersion of a protein or a polypeptide to a pH of from 2–12 such that a net electrical charge exists between said protein or polypeptide and said whole microbial cells when said whole cell dispersion and said polypeptide or protein dispersion are combined;
    mixing said dispersions of whole microbial cells and protein or polypeptide;
    casting said mixed dispersions into a membrane; and
    drying said membrane, whereby bonding occurs between said cells and polypeptide or protein by the accumulative effect of multiple hydrogen bonds, salt linkages and van der Walls interactions, wherein the bonding forces effect immobilization of said whole microbial cells to the protein or polypeptide of said membrane.

2. The process of claim 1 wherein the dry thickness of said membrane is from 0.005 mm to 0.1 mm.

3. The process of claim 1, wherein said protein is collagen or zein.

4. The process of claim 1 wherein said membrane is layered on a self-supporting base.

5. The process of claim 1 wherein the protein is collagen and wherein the membrane is tanned.

6. The process of claim 1 wherein said protein is collagen.

* * * * *

UNITED STATES PATENT AND TRADEMARK OFFICE
CERTIFICATE OF CORRECTION

PATENT NO. : 3,972,776
DATED : August 3, 1976
INVENTOR(S) : VIETH ET AL

It is certified that error appears in the above-identified patent and that said Letters Patent are hereby corrected as shown below:

Column 2, line 12, delete "attached" and insert --attacked--.

Column 3, line 14, delete "easly" and insert --easily--.

Column 3, line 34, delete "catlytic" and insert --catalytic--.

Column 4, line 36, delete "steriod" and insert --steroid--.

Column 4, line 45, delete "of" and insert --or--.

Column 10, line 4, delete "VISKON" and insert --VISKON®--.

Column 11, line 11, delete "phaechromogenes" and insert --phaeochromogenes--.

Column 12, line 8, delete "protoelytic" and insert --proteolytic--

Signed and Sealed this

Twenty-ninth Day of November 197

[SEAL]

Attest:

RUTH C. MASON
*Attesting Officer*

LUTRELLE F. PARKER
*Acting Commissioner of Patents and Trademark*